United States Patent [19]

Gras et al.

[11] 4,302,351

[45] Nov. 24, 1981

[54] COMPOUNDS CONTAINING ISOCYANURIC GROUPS AND TERMINALLY BLOCKED ISOCYANATE GROUPS

[75] Inventors: Rainer Gras; Elmar Wolf, both of Herne, Fed. Rep. of Germany

[73] Assignee: Chemische Werke Huls Aktiengesellschaft, Marl, Fed. Rep. of Germany

[21] Appl. No.: 139,399

[22] Filed: Apr. 11, 1980

Related U.S. Application Data

[63] Continuation of Ser. No. 889,217, Mar. 23, 1978, abandoned.

[30] Foreign Application Priority Data

Mar. 24, 1977 [DE] Fed. Rep. of Germany ....... 2712931

[51] Int. Cl.³ .................. C08G 18/80; C09K 3/00; C07D 251/34
[52] U.S. Cl. .................. 252/182; 260/239.3 R; 528/45
[58] Field of Search ............... 252/182; 260/239.3 R; 528/45

[56] References Cited

U.S. PATENT DOCUMENTS

| | | | |
|---|---|---|---|
| 3,577,391 | 5/1971 | Argabright et al. | 528/45 |
| 3,822,240 | 7/1974 | Schmitt et al. | 528/45 X |
| 3,893,977 | 7/1975 | Wingler | 528/45 |
| 3,919,218 | 11/1975 | Schmitt et al. | 544/222 |
| 4,088,637 | 5/1978 | Zecher et al. | 528/45 |
| 4,150,211 | 4/1979 | Muller et al. | 528/45 |

*Primary Examiner*—Dolph H. Torrence
*Attorney, Agent, or Firm*—Oblon, Fisher, Spivak, McClelland & Maier

[57] ABSTRACT

Method for the preparation of compounds containing isocyanuric groups and blocked isocyanate groups from aliphatic and/or cycloaliphatic polyisocyanates; wherein the starting polyisocyanate is first transformed by a known method into a mixture containing an isocyanurate containing at least two free isocyanate groups; and this intermediate product is reacted with monofunctional acidic-hydrogen containing blocking agents; wherein the blocking agent is added in an amount such that one equivalent of agent is added for every equivalent of NCO-group equivalent.

5 Claims, 4 Drawing Figures

COMPOUNDS CONTAINING ISOCYANURIC GROUPS AND TERMINALLY BLOCKED ISOCYANATE GROUPS

This is a continuation of application Ser. No. 889,217, filed Mar. 23, 1978, abandoned.

BACKGROUND OF THE INVENTION

1. Field of the Invention

The present invention relates to a method for the preparation of new compounds with built-in isocyanuric groups as well as with the compounds obtained by this method.

2. Description of the Prior Art

The preparation of masked isocyanates, also called isocyanate yielders, is known and is described in Houben-Weyl, Methoden der organischen Chemie, XIV/2 pp. 61–70. It is known to use as blocking agents, tertiary alcholos, phenols, acetoacetic ester, malonic acid ester, acetyl acetonate, phthalimide, imidazole, hydrogen chloride, hydrogen cyanide and ε-caprolactam.

These masked isocyanates possess the property of reacting, at higher temperatures, as isocyanates. The splitting of the masking group is easier, the more acidic the hydrogen atom of the masking group. Such blocked isocyanates are described in the DT-OS 21 66 423. Terminally blocked isocyanates, which also contain in addition uretidione groups, are described in DT-OS 25 02 934.

Surprisingly, the literature does not contain any reference to isocyanuric groups containing terminally blocked isocyanate groups with aliphatic polyisocyanates. Blocked aromatic isocyanurates are reported for the preparation of heat resistant grinding resistant urethane-enamel, especially for electric wire insulators, in JA-AS No. 73-30453, filed on Dec. 24, 1969. The preparation of aliphatic polyisocyanate-containing thus blocked isocyanuric groups is on the other hand, unknown until now.

SUMMARY OF THE INVENTION

It is an object of the invention to present a method for the preparation of compounds containing blocked isocyanate groups and isocyanuric groups from an aliphatic and/or cycloaliphatic polyisocyanate, wherein said aliphatic and/or cycloaliphatic polyisocyanate is, in known fashion, transformed into a mixture consisting of an isocyanurate containing at least two free isocyanate groups and then this intermediate product is treated with monofunctional, acidic-hydrogen containing blocking agents at 50°–120° C., wherein the blocking agent is added so that one equivalent of blocking agent is added for every equivalent of NCO group-equivalent.

A variation of this method consists in freeing the intermediate product from monomeric polyisocyanate and then, the practically monomer-free polyisocyanate is blocked in the described fashion. Especially advantageous as a monofunctional, acid hydrogen-containing blocking agent is ε-caprolactam.

Another object of the invention is to describe compounds containing blocked isocyanate groups and isocyanuric groups which consist of at least of an isocyanurate containing at least two isocyanate groups blocked with ε-caprolactam and if necessary a monomeric isocyanate blocked with ε-caprolactam added to complement the 100% weight, with a content of unblocked NCO groups of less than 0.5% by weight.

DESCRIPTION OF THE PREFERRED EMBODIMENTS

Figure 1:
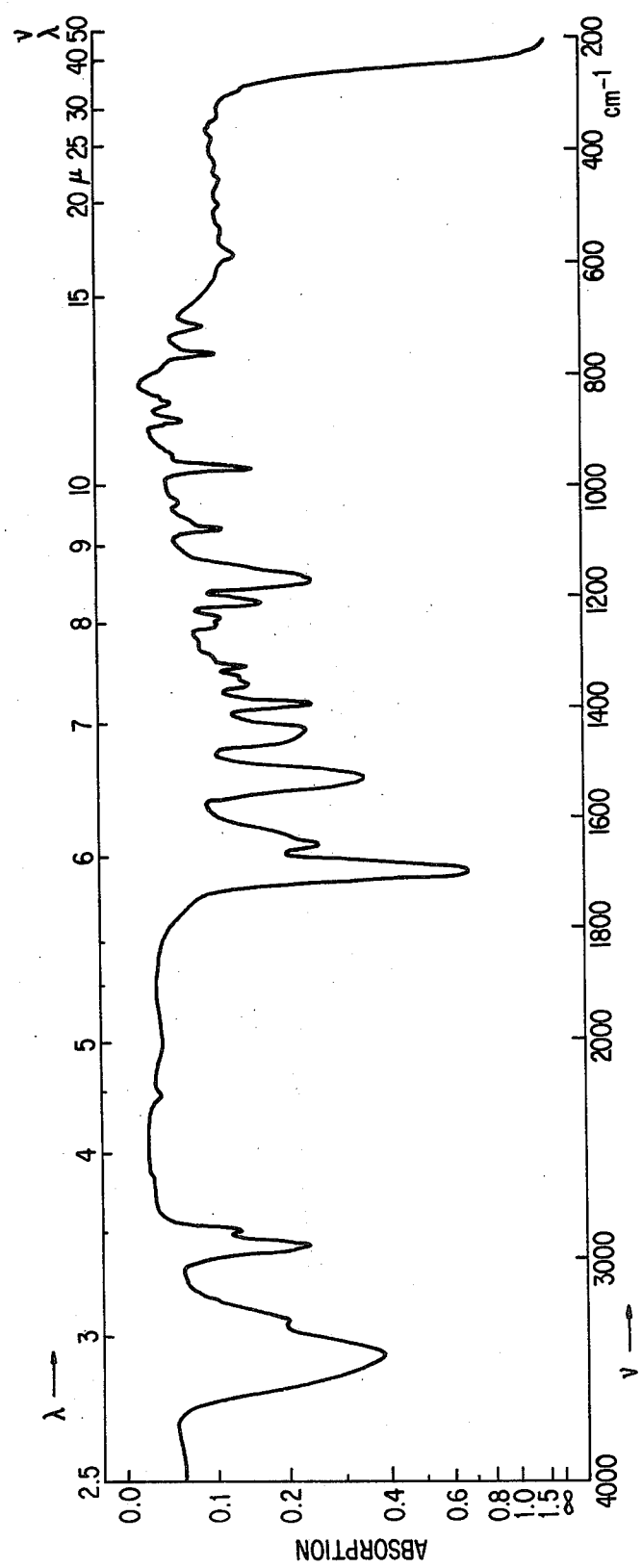
FIG. 1 shows the IR-spectrum of the product obtained in Example 4.

Suitably, the monomeric polyisocyanate is identical with the one used for the preparation of the isocyanurate. Especially advantageous, because of its good optical properties, is monomeric 3-isocyanatomethyl-3,5,5-tri-methylcyclohexylisocyanate and as the isocyanurate, the thus resulting oligomerization products. The isocyanurate can also be a mixture of the trimeric and higher addition products of the monomeric polyisocyanate. The isocyanurate group content of the prepared compounds according to the present invention is of 2–14% by weight.

For the preparation of the isocyanuric isocyanates, that is to say for the trimerization reaction, it is possible to use for example polyisocyanates, especially diisocyanates such as cycloaliphatic and/or araliphatics, i.e. aryl substituted aliphatic diisocyanates, such as the ones exemplified in the article of W. Siefken in Justus Liebigs Annalen de Chemie 562, pages 75–136; such as 1,2-ethylenediisocyanate, 1,4-tetramethylenediisocyanate, 1,6-hexamethylenediisocyanate, 2,2,4- or 2,4,4-trimethyl-1,6-hexamethylenediisocyanate (TMDI), 1,12-dodecanediisocyanate, ω,ω'-diisocyanatodipropylether, cyclobutane-1,3-diisocyanate, cyclohexane-1,3- and 1,4-diisocyanate, 3-isocyanatomethyl-3,5,5-trimethylcyclohexylisocyanate, also known as isophorondiisocyanate and abbreviated as IPDI, hexahydro-1,3- and -1,4-phenylene-diisocyanate, 2,4- and 2,6-hexahydrotoluylenediisocyanate, perhydro-2,4'- and/or -4,4'-diphenylmethane-diisocyanate, ω,ω'-diisocyanato-1,4-diethylbenzene as well as appropriate mixtures of these isomers. Further appropriate isocyanates are described in the aforementioned article in the Annalen at page 122 and following.

Especially convenient are the technically readily accessible aliphatic or cycloaliphatic diisocyanates, such as 3-Isocyanatomethyl-3,5,5-trimethylcyclohexylisocyanate, 2,4- and 3,6-hexahydrotoluylenediisocyanate, perhydro-2,4'- and/or -4,4'-diphenylmethandiisocyanate and 1,6-hexamethylene-diisocyanate as well as their isomeric mixtures.

During the trimerization of the polyisocyanates it is also possible to use under certain limiting conditions, aliphatic and/or cycloaliphatic monoisocyanates comparable to the above-mentioned polyisocyanates; so long as the formed isocyanuric isocyanate contains at least two free isocyanate groups in the medium.

The starting materials for the procedures of the present invention are then subject to trimerization under well known conditions, such as those exemplified in the GB-PS No. 1 391 066 and DT-OS No. 2 325 826. The trimerization of the described aliphatic or cycloaliphatic isocyanates is a catalytic reaction. It is possible to use as catalysts, metallic compounds of the salt and base groups and homopolar metallic compounds such as metal-naphthenate, sodium benzoate in DMF, alkali earth acetate, -formate and -carbonate, metal-alkoxide, AlCl₃ and Fe-acetylacetonate, as well as aziridine and its derivatives as a catalyst and trialkylamine with 1 to 5 carbon atoms in the alkyl groups as cocatalysts. Especially useful for the trimerization of aliphatic isocyanates is the previously proposed catalytic system composed of N,N'-endoethylenpiperazine and propylenoxide. The trimerization can be carried out without solvent or in the presence of an inert organic solvent. To carry out the trimerization method it is essential to quench the reaction, and especially advantageous when 10 to 30% of the NCO groups have reacted to trimerize. The unreacted isocyanate is then separated from the formed isocyanurate through a vacuum destillation.

In the procedures of the present invention, it is possible to react the thus accessible isocyanuric isocyanates either as nonisocyanate containing components or as a mixture with isocyanurate-free polyisocyanates. The addition of isocyanuric group-free polyisocyanates allows, in a simple way to vary, according to will the properties of the products of this process, especially their melting point.

It is particularly advantageous, in the process of the present invention, to use as the isocyanurate component, the aforementioned triisocyanate-mixture prepared in situ, which is accessible through the partial trimerization of an appropriate diisocyanate.

Once the polyisocyanurates containing isocyanate groups especially triisocyanates, or their mixtures with isocyanurate group-free polyisocyanates, especially diisocyanates are obtained, these are then used as intermediates in the preparation of the products prepared by the method of the present invention.

In a further step of the method of the present invention, the products from the intermediate step are, as described hereinafter, transformed without further modification into the products of the present method, having isocyanurate groups and terminally blocked isocyanate groups.

Appropriate blocking agents for the methods of the present invention are monofunctional, acidic-hydrogen-containing compounds containing a group reactive towards isocyanate groups, which will react with said isocyanate groups at temperatures above 50° C., preferably between 80°–120° C.; which will undergo an addition reaction; and so that the thus obtained addition products, upon mixing with nonvolatile polyols having hydroxy groups will react, at temperatures between 100° and 200° C., with liberation of the blocking agent, with said polyoles and form urethanes.

Appropriate blocking agents are for example secondary or tertiary alcohols, such as isopropanol or t-butanol, oximes, such as formaldoxime, acetaldoxime, methylethylketonoxime, cyclohexanonoxime, trimethylcyclohexanonoxime, 2,2,6,6-Tetra-methyl-piperidon-(4)-oxime, acetophenonoxime, benzophenonoxime, or diethylglyoxime, lactams, such as ε-caprolactam, δ-valerolactam, γ-butyrolactam, hydroxamic acids or their esters, such as acetohydroxamic acid, benzohydroxamic acid; phenols, such as phenol, o-methylphenol, p-dimethylaminophenol; N-alkylamide, such as methyl-acetamide and imidazols, such as 2-methylimidazol.

Especially advantageous for the methods of the present invention are blocking agents of the following formula:

X—H;

wherein X stands for

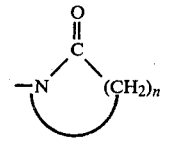  n = 3–7

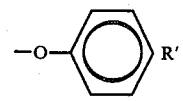

R: H, CH₃, C₉H₁₉
R': R

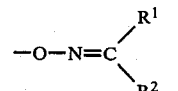

R¹: H, C$_n$H$_{2n+1}$
R² = R¹ (n = 2–5)

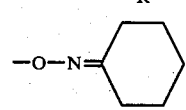

In order to carry out the blocking reaction, it is generally useful to add the blocking reagent to the isocyanate component. The reaction can be carried out with or without the presence of appropriate (inert) solvents. The blocking reaction is generally carried out at 80°–120° C. The blocking reagent is added in such amounts, so that for each NCO-group equivalent, there is one equivalent of blocking reagent. It is also possible to use the accelerating catalysts, useful for the isocyanate-poly addition reaction, such as tin (II)-octanoate. The catalysts are added as a rule in an amount between 0.001 and 1% by weight with reference to the amount of the agent containing the active hydrogen atoms reactive towards isocyanate.

The products prepared by the method of the present invention, are generally compounds with molecular weight in the ranges 300–3000, preferably 400–2000. The products obtained by these methods have melting points or melting ranges of from 30° to 200° C., especially 60°–170° C. The aforementioned polyisocyanates of the present invention, containing isocyanurate groups are characterized by a isocyanurate group content (calculated as (OCN—)₃) of from 2% weight to 14% weight, preferably of from 3–10% weight and a content of end blocked available isocyanate groups (calculated as NCO) of from 2–18, preferably 10–17% by weight.

The compounds of the present invention are especially useful because of their low melting points and concomitant higher molecular weights, as cocatalysts for the anionic polymerization of ε-caprolactam.

Having generally described the invention, a more complete understanding can be obtained by reference to certain examples, which are included for purposes of illustration only and are not intended to be limiting unless otherwise specified.

EXAMPLE 1 a. Preparation of the Triisocyanurate 1000 parts by weight of isophorondiisocyanate (IPDI) were heated at 120° C. for 3 hours in the presence of 0.5% by weight of the catalyst system composed of 1,4-diazabicyclooctan-(2.2.2) (also called Dabco ®) and propylenoxide-1,2 (weight ratios: Dabco:-

Propylenoxide = 1:2). At this point, the original NCO-content of the starting material fell from 37.8 to about 28% NCO. It was then quickly cooled to room temperature, at which the NCO content only changes negligibly even after several weeks. The reaction mixture which is still low in viscosity, was then subjected to a vacuum distillation without further deactivation of the catalyst. The monomer, distilled at 150°–160° C. and 0.1 Torr. The residue had a NCO-content of 17.9% by weight, and assuming that besides of the trimer formation there also occurred some pentameric (IPDI) formation then one can calculate the weight ratio of trimer:pentamer as 71:29.

This monomer-free isocyanatoisocyanurate has a melting range of 86°–89° C.

b. Blocking of the Triisocyanurate

To 100 parts per weight of this monomer free isocyanatoisocyanurate mixture were added at 150° C., 48.1 parts per weight of ε-caprolactam slowly and under intensive stirring. The addition was regulated so that the reaction temperature never rose above 160° C. In order to allow the reaction to go to completion, it was kept for a further two hours at 150° C.

| Average molecular weight | about 1180* |
|---|---|
| Free NCO (%) | less than 0.5 |
| Blocked NCO (%) | 12.08 |
| Melting range | 140–160° C. |
| Decomposition Temperature | about 170° C. |
| Glass Transition Temperature (DTA) | 70–90° C. |

*The analysis of the average molecular weight follows from the experimentally determined NCO percents, which are representative for the average molecular weight of the isocyanates, and a calculated increment for the equivalent amounts of the blocking agents.

EXAMPLE 2 a. Preparation of the Triisocyanurate 100 parts per weight of isophorondiisocyanate (IPDI) were heated with 0.5 parts per weight of the catalyst of example 1 for 0.5 hours at 120° C. The NCO content showed after this time a value of 35.8%. In order to deactivate the catalyst, the reaction mixture was heated for 15 minutes at 120° C. and 20 Torr. During this time the NCO content of reaction mixture fell further to 35%.

b. Blocking of the Triisocyanurate

To 100 parts per weight of this isocyanatoisocyanurate mixture were added at 90° C., 94.1 parts per weight of ε-caprolactam in such a way that the reaction temperature never rose above 110° C. To run the reaction to completion it was kept for further two hours at 120° C.

| Average molecular weight | about 480 |
|---|---|
| Free NCO (%) | less than 0.5 |
| Blocked NCO (%) | 18.02 |
| Melting range | 55–60° C. |
| Decomposition Temperature | about 175° C. |
| Glass Transition Temperature (DTA) | 25–42° C. |

EXAMPLE 3 a. Preparation of the Triisocyanurate 100 parts per weight of IPDI were heated with 0.5 parts per weight of the catalyst described in Example 1a for 1 hour at 120° C. The NCO content after this period of time was 31.7%. The deactivation of the catalyst was carried out in an analogous fashion to that of Example 2a.

The NCO content of the deactivated reaction mixture was determined to be 31.0%.

b. Blocking of the Triisoyanurate

To 100 parts per weight of this isocyanatoisocyanurate mixture were added at 100° C., 83.4 parts per weight of ε-caprolactam in such a way that the temperature of the reaction mixture never rose above 120° C.

To run the reaction to completion it was heated for further 2 to 3 hours to 130° C.

| Average molecular weight | about 535 |
|---|---|
| Free NCO (%) | less than 0.5 |
| Blocked NCO (%) | 16.90 |
| Melting range | 68–71° C. |
| Decomposition Temperature | about 170° C. |
| Glass Transition Temperature (DTA) | 28–48° C. |

EXAMPLE 4 a. Preparation of the Triisocyanurate 100 parts per weight of isophorondiisocyanate (IPDI) were heated with 0.5 parts per weight of a catalyst system as described in Example 1a for 3 hours at 120° C. During this time the NCO content fell from 37.8% (corresponding to 100% IPDI) to 28.4% (50% IPDI reacted). For the deactivation of the catalyst, the reaction mixture was cooled to 40° C. and at this temperature was stripped for ½ hour with nitrogen. The NCO content of the reaction mixture changed further to 28.2%.

b. Blocking of the Triisocyanurate

To 100 parts per weight of this isocyanato-isocyanurate mixture was added at 100° C., 75.8 parts per weight of ε-caprolactam in portions so that the reaction temperature never rose above 110° C. To run the reaction to completion it was held for further 2 hours at 120° C.

| Average molecular weight | about 590 |
|---|---|
| Free NCO (%) | less than 0.5 |
| Blocked NCO (%) | 16.03 |
| Melting range | 75–80° C. |
| Decomposition Temperature | about 170° C. |
| Glass Transition Temperature (DTA) | 30–55° C. |

The IR-spectrum of the reaction product is shown in FIG. 1.

EXAMPLE 5 a. Preparation of the Triisocyanurate 100 parts per weight of IPDI were heated with 0.75 parts per weight of a catalyst system as described in Example 1a for 2 hours at 120° C. During this time the NCO content fell from 37.8% to 29.4%. To deactivate the catalyst, the reaction mixture was evacuated at 120° C. for 15 minutes at 30 Torr. During this time the NCO content of reaction mixture changed further to 27%.

b. Blocking of the Triisocyanurate

To 100 parts per weight of this isocyanatoisocyanurate mixture were added in portions at 110° C., 72.6 parts per weight of ε-caprolactam so that the reaction temperature never rose above 120° C. To run the reaction to completion it was kept for further 2 hours at 120° C.

| | |
|---|---|
| Average molecular weight | about 620 |
| Free NCO (%) | less than 0.5 |
| Blocked NCO (%) | 15.64 |
| Melting range | 80–89° C. |
| Decomposition Temperature | about 172° C. |
| Glass Transition Temperature (DTA) | 34–60° C. |

Figure 2:
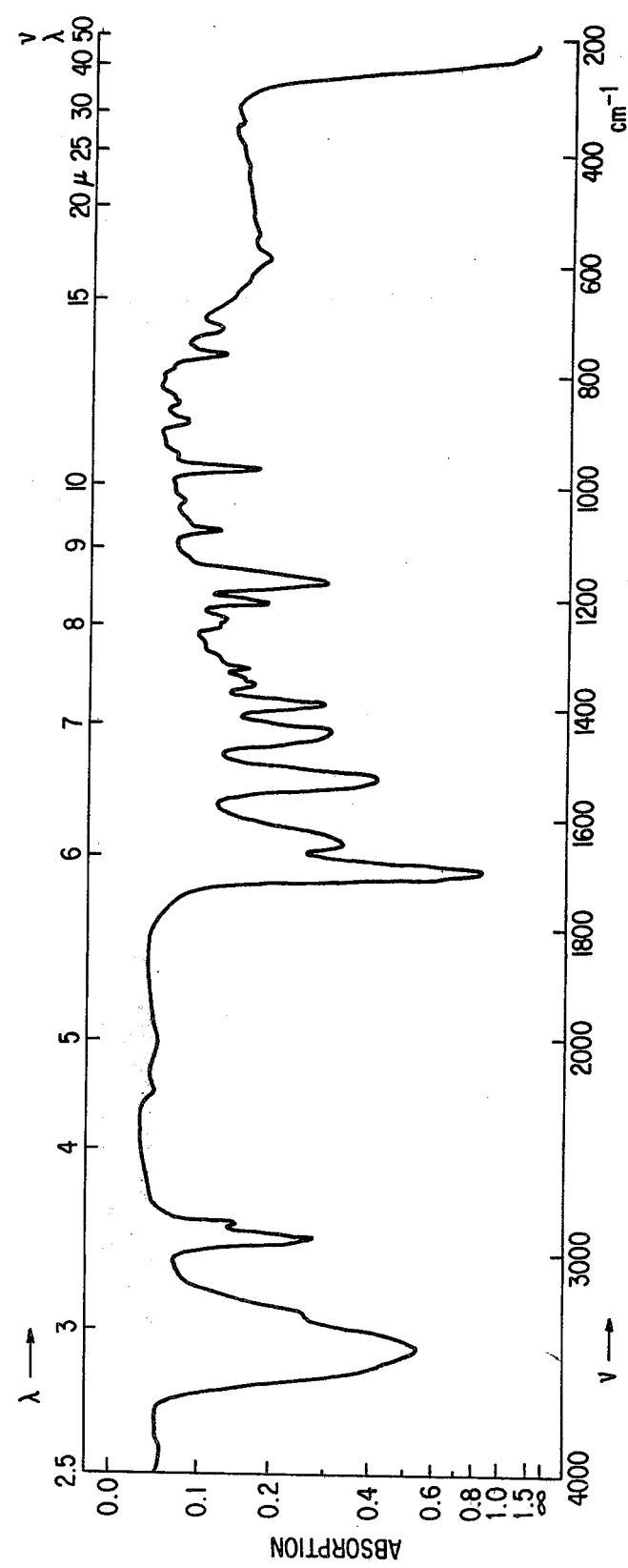
FIG. 2 shows the IR spectrum of the product obtained in Example 5.

The IR-spectrum of reaction product is shown on FIG. 2.

EXAMPLE 6 a. Preparation of the Triisocyanurate 100 parts per weight of IPDI were heated with 0.5 parts per weight of the catalyst described in Example 1 for 4.5 hours at 120° C. The progress of the trimerization was followed with the aid of the index of refraction, the vecosity or the NCO content. At an NCO content of 25.8%, the reaction was evacuated for ½ hour at 20 Torr. After cooling the reaction mixture, it had an NCO content of 25%.

b. Blocking of the Triisocyanurate

To 100 parts per weight of this isocyanatoisocyanurate mixture were added in portions, at 120° C., 67.3 parts per weight of ε-caprolactam slowly, with good stirring. After addition of ε-caprolactam was completed the reaction mixture was further heated for 1 hour at 130° C.

| | |
|---|---|
| Average molecular weight | about 680 |
| free NCO (%) | less than 0.5 |
| Blocked NCO (%) | 14.95 |
| Melting range | 85–95° C. |
| Decomposition Temperature | about 170° C. |
| Glass Transition temperature | 40–62° C. |

Figure 3:
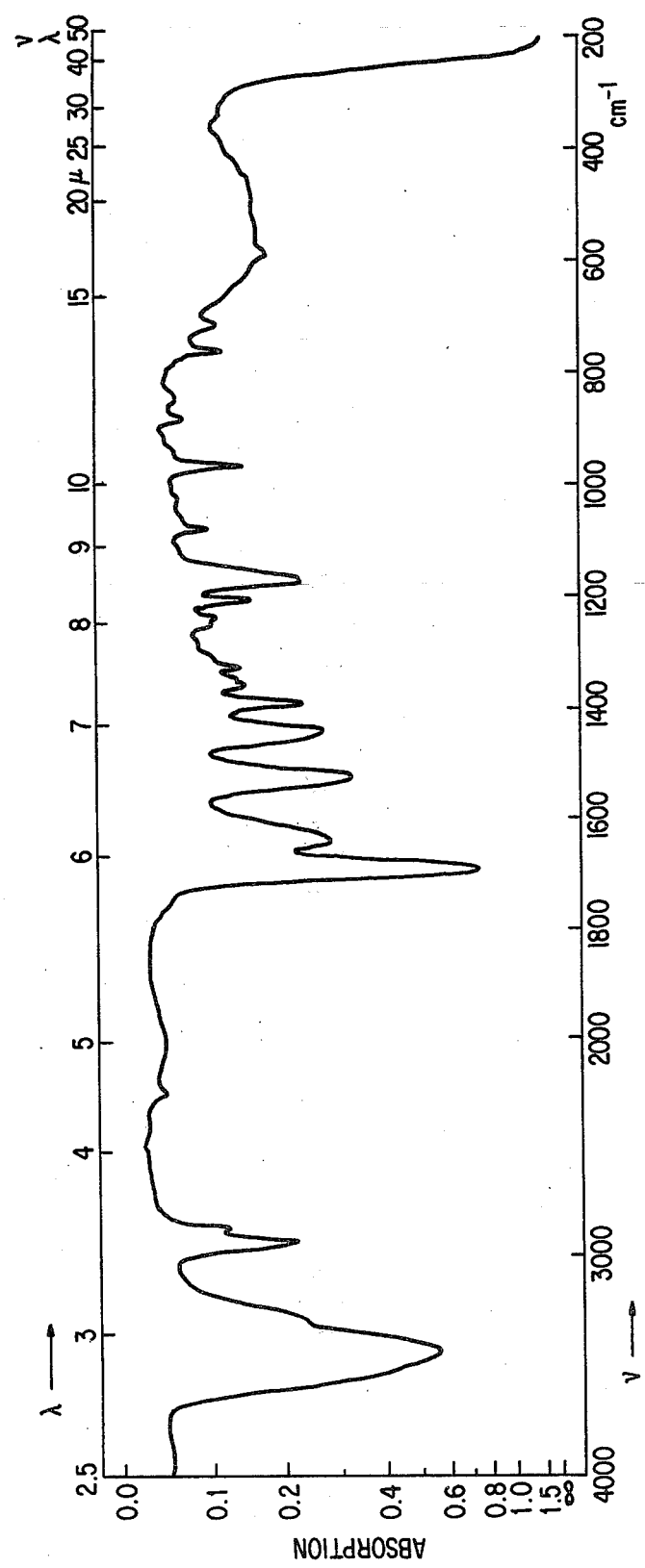
FIG. 3 shows the IR spectrum of the product obtained in Example 6.

The IR-spectrum of reaction product is shown in FIG. 3.

EXAMPLE 7 a. Preparation of the Triisocyanurate

An isocyanatoisocyanurate mixture was prepared from IPDI according to the method of Examples 2a–4a, having an NCO content of 22.9%.

b. Blocking of the Triisocyanurate

To 100 grams of this mixture (NCO: 22.9%) were added in portions at 130° C., with intensive stirring, 61.6 parts per weight of ε-caprolactam, so that the reaction temperature of the mixture could be held at 130° C. After the addition of ε-caprolactam was complete, the reaction was run to completion by heating for further 2 hours at 130° C.

| | |
|---|---|
| Average molecular weight | about 760 |
| Free NCO (%) | less than 0.5 |
| Blocked NCO (%) | 14.17 |
| Melting range | 100–105° C. |
| Decomposition Temperature | about 170° C. |
| Glass Transition Temperatures (DTA) | 42–70° C. |

Figure 4:
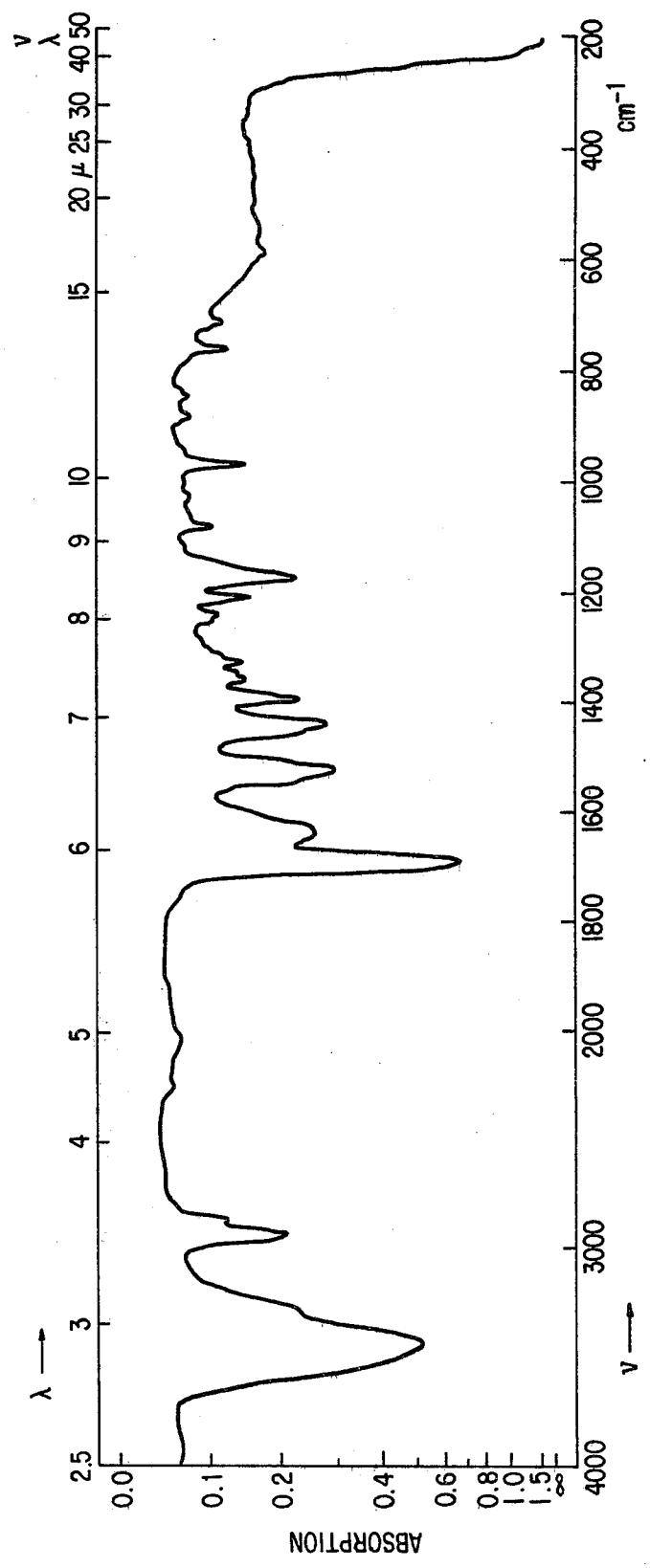
FIG. 4 shows the IR spectrum of the product obtained in Example 7.

The IR-spectrum of the reaction product is shown in FIG. 4.

EXAMPLE 8 a. Preparation of the Triisocyanurate

An isocyanatoisocyanurate mixture (with deactivated catalyst) was prepared from IPDI according to the methods of Examples 2a–4a, having an NCO content of 20.9%.

b. Blocking of the Triisocyanurate

To 100 parts per weight of this mixture (NCO: 20.9%) were added with intensive stirring at 140° C., 56.2 parts per weight of ε-caprolactam so that the reaction temperature of the mixture could be held at 140° C. After the addition of ε-caprolactam was complete, the reaction was run to completion by heating for further 1 hour at 140° C.

| | |
|---|---|
| Average molecular weight | about 860 |
| Free NCO (%) | less than 0.5 |
| Blocked NCO (%) | 13.33 |
| Melting range | 110–119° C. |
| Decomposition temperature | about 170° C. |
| Glass Transition Temperature (DTA) | 50–75° C. |

EXAMPLE 9 a. Preparation of the Triisocyanurate 100 parts per weight of 2.4.4-(2.2.4)-trimethylhexamethylenediisocyanate (TMDI) were heated with 0.5 parts per weight of a catalyst system consisting of 2 parts per weight of propylenoxide and 1 part per weight of Dabco for 2 hours at 120° C. During this time the NCO content fell from 40% (pure TMDI) to 29.5%. To deactivate the catalyst, the reaction mixture was evacuated for 0.5 hours at 30 Torr. After cooling to a room temperature, the reaction mixture had an NCO content of 28.7%.

b. Blocking of the Triisocyanurate

To 100 parts per weight of this mixture (NCO content: 28.7%) were added at 100° C., 77.2 parts per weight of ε-caprolactam so that the reaction temperature never rose above 110° C. After the addition of ε-caprolactam was complete, the reaction was run to completion by heating for further 2 hours at 120° C.

| | |
|---|---|
| Average molecular weight | about 660 |
| Free NCO (%) | less than 0.5 |
| Blocked NCO (%) | 16.2 |
| Viscosity (cp) at room temperature | $1.7 \times 10^6$ |
| 40° C. | $7 \times 10^5$ |
| 60° C. | $4 \times 10^4$ |
| 80° C. | $4 \times 10^3$ |
| Decomposition temperature °C. | about 170 |

EXAMPLE 10 a. Preparation of the Triisocyanurate

An isocyanatoisocyanurate mixture (with deactivated catalyst) is prepared from TMDI according to the method of Example 1a, having an NCO content of 18.1%.

b. Blocking of the Triisocyanurate

To 100 parts per weight of this isocyanatoisocyanurate mixture were added at 120° C., 48.7 parts per weight of ε-caprolactam slowly so that the temperature never rose above 130° C. After the addition of ε-caprolactam was complete, the reaction mixture was allowed to go to completion by heating for further 1 hour at 130° C.

| | |
|---|---|
| Average molecular weight | about 1270 |
| Free NCO (%) | less than 0.5 |
| Blocked NCO (%) | 12.17 |
| Melting range | 58–62° C. |
| Decomposition Temperature | about 170° C. |
| Glass Transition Temperature (DTA) | 25–40° C. |

What is claimed and intended to be covered by Letters Patent of the United States is:

1. A mixture containing isocyanurate and blocked isocyanate groups which comprises:
    at least 10% by weight of an isocyanurate derived from a polyisocyanate selected from the group consisting of 3-isocyanatomethyl-3,5,5-trimethyl-cyclohexylisocyanate, 2,4,4-trimethyl-hexamethylenediisocyanate, and 2,2,4-trimethyl-hexamethylenediisocyanate, containing at least two isocyanate groups blocked with ε-caprolactam; and
    a monomeric polyisocyanate blocked with ε-caprolactam in such amounts as necessary to complete 100% by weight of said mixture; and wherein the unblocked NCO-group content of said mixture is less than 0.5% by weight.

2. The mixture of claim 1 wherein said monomeric polyisocyanate is identical with the polyisocyanate used for the preparation of said isocyanurate.

3. The mixture of claim 2 wherein the monomeric polyisocyanate is 3-isocyanatomethyl-3,5,5-trimethyl-cyclohexylisocyanate.

4. The mixture of claim 2 wherein said monomeric polyisocyanate is a 1:1 isomeric mixture of 2,2,4- and 2,4,4-trimethyl-1,6-hexamethylenediisocyanate.

5. The mixture of claim 1 wherein said isocyanurate containing said blocked isocyanate groups, is a mixture of the trimerization product and higher oligomerization products of said monomeric polyisocyanate.

* * * * *